United States Patent
Ferrari et al.

(10) Patent No.: US 7,450,779 B2
(45) Date of Patent: Nov. 11, 2008

(54) DE-NOISING DIGITAL RADIOLOGICAL IMAGES

(75) Inventors: Ricardo J. Ferrari, Edmonton (CA); Robin Winsor, Calgary (CA)

(73) Assignee: Imaging Dynamics Company Ltd., Calgary, Alberta (CA)

(*) Notice: Subject to any disclaimer, the term of this patent is extended or adjusted under 35 U.S.C. 154(b) by 479 days.

(21) Appl. No.: 11/131,286

(22) Filed: May 18, 2005

(65) Prior Publication Data

US 2005/0259889 A1 Nov. 24, 2005

Related U.S. Application Data

(60) Provisional application No. 60/573,287, filed on May 21, 2004.

(51) Int. Cl.
G06K 9/40 (2006.01)
G06K 9/00 (2006.01)
(52) U.S. Cl. .................................. 382/275; 382/128
(58) Field of Classification Search ................. 382/275, 382/128–132, 254, 274; 600/310
See application file for complete search history.

(56) References Cited

U.S. PATENT DOCUMENTS 5,309,496 A 5/1994 Winsor

OTHER PUBLICATIONS

Ye, Zhen; Lu, Cheng-Chang; A Complex Wavelet Domain Markov Model for Image Denoising; Sep. 14-17, 2003; IEEE; vol. 3; p. 365-368.*

Mascarenhas, Nelson D. A.; Furuie, Sergio S.; Portal, Angel L. S.; Global Projection Estimation Methods for the Tomographic Reconstruction of Images with Poisson Noise; Dec. 1993; IEEE Transactions on Nuclear Science; vol. 40, No. 6; p. 2008-2013.*

Bradley, A (2003) Shift-invariance in discrete wavelet transform. In: Sun et al Proceedings of the Seventh Digital Image Computing: Techniques and Applications p. 29-38.

Crouse et al (1998) Wavelet-based statistical signal processing using hidden Markov models. IEEE Transactions on Signal Processing 46:886-902.

Dippel et al (2002) Multiscale contrast enhancement for radiographies: Laplacian pyramid versus fast wavelet transform. IEEE Transactions on Medical Imaging 21:343-353.

Donoho (1995) De-noising by soft-thresholding. IEEE Transactions on Information Theory 41:613-627.

Donoho et al (1995) Adapting to unknown smoothness via wavelet shrinkage. Journal of American Statistical Association 90:1200-1224.

(Continued)

*Primary Examiner*—Aaron W Carter
(74) *Attorney, Agent, or Firm*—Gowling LaFleur Henderson LLP; D. Doak Horne; Brian Y. Lee

(57) ABSTRACT

This invention relates to a method for de-noising digital radiographic images based upon a wavelet-domain Hidden Markov Tree (HMT) model. The method uses the Anscombe's transformation to adjust the original image to a Gaussian noise model. The image is then decomposed in different sub-bands of frequency and orientation responses using a dual-tree complex wavelet transform, and the HMT is used to model the marginal distribution of the wavelet coefficients. Two different methods were used to denoise the wavelet coefficients. Finally, the modified wavelet coefficients are transformed back into the original domain to get the de-noised image.

14 Claims, 14 Drawing Sheets

OTHER PUBLICATIONS

Durand et al (2001) Artifact free signal de-noising with wavelets. In: International Conference in Acoustics, Speech and Signal Processing. p. 3685-3688.

Kingsbury (1999) Image processing with complex wavelets. Philosophical Transactions of the Royal Society of London 357:2543-2560.

Laine et al (1994) Mammographic feature enhancement by multiscale analysis. IEEE Transactions on Medical Imaging 13:725-740.

Romberg et al (2001) Bayesian tree-structured image modeling using wavelet-domain hidden Markov models. IEEE Transactions on Image Processing 10:1056-1068.

* cited by examiner

DE-NOISING DIGITAL RADIOLOGICAL IMAGES

RELATED APPLICATION

Priority is claimed from U.S. provisional application 60/573,287 filed May 21, 2004, entitled DE-NOISING DIGITAL RADIOLOGICAL, listing Ricardo J. Ferrari and Robin Winsor as inventors, such provisional application incorporated herein by reference.

FIELD OF THE INVENTION

This invention relates generally to de-noising digital radiological images.

BACKGROUND OF THE INVENTION

General image de-noising techniques based upon the traditional (orthogonal, maximally-decimated) discrete wavelet-transform (DWT) have proved to provide the state-of-the-art in de-noising performance, in terms of peak signal-to-noise ratio (PSNR), according to many papers presented in the literature, e.g. Crouse M, Nowak R, Baraniuk R (1998) Wavelet-based statistical signal processing using hidden Markov models. IEEE Transactions on Signal Processing 46:886-902, Donoho D (1995) De-noising by soft-thresholding; IEEE Transactions on Information Theory 41:613-627, and Romberg J, Choi H, Baraniuk R (2001) Bayesian tree-structured image modeling using wavelet-domain hidden Markov models; and, IEEE Transactions on Image Processing 10:1056-1068. The basic idea behind this image-de-noising approach is to decompose the noisy image by using a wavelet transform, to shrink or keep (by applying a soft or hard thresholding technique) wavelet coefficients which are significant relative to a specific threshold value or the noise variance and to eliminate or suppress insignificant coefficients, as they are more likely related to the noise. The modified coefficients are then transformed back into the original domain in order to get the denoised image.

Despite the high PSNR values, most of these techniques have their visual performance degraded by the introduction of noticeable artifacts which may limit their use in de-noising of medical images. The common cause of artifacts in the traditional wavelet-based de-noising techniques is due to the pseudo-Gibbs phenomenon which is caused by the lack of translation invariance of the wavelet method. Shift variance results from the use of critical sub-sampling (decimation) in the DWT. Consequently, the wavelet coefficients are highly dependent on their location in the sub-sampling lattice which directly affects the discrimination of large/small wavelet coefficients, likely related to singularities/non-singularities, respectively. Although this problem can be avoided by using an undecimated DWT, it is too computationally expensive.

SUMMARY OF THE INVENTION

It is an object of the invention to provide a digital image de-noising method that improves upon currently available methods. One particular object of the invention is to provide an effective de-noising method for digital radiological images that is computationally tractable.

According to one aspect of the invention, there is provided a method of de-noising a digital radiological image. The method comprises a training stage comprising:

(a) obtaining a digital radiological image of a phantom;
(b) applying a direct wavelet transformation to the phantom image to obtain wavelet coefficients of the phantom image;
(c) estimating parameters of a noise and background distribution and a singularity distribution that together fits an observed overall distribution of the wavelet coefficients, then,
(d) saving the estimated parameters.

After training, the de-noising method is applied to a digital radiological image of a subject, as follows: first, apply a direct wavelet transformation to the subject image to obtain wavelet coefficients of the subject image; then, use the saved estimated parameters to shrink or threshold the wavelet coefficients of the subject image to reduce noise components; finally, apply an inverse wavelet transformation to the shrunk or thresholded wavelet coefficients to obtain a de-noised subject image.

A dual-tree complex wavelet transform can be used to execute the direct wavelet transformation of both the phantom image and the subject image. A Hidden Markov Tree (HMT) model can be used to estimate the parameters of a noise and background distribution and a singularity distribution that together fits the observed overall distribution of the wavelet coefficients. Where a HMT model is used, the subject image can be first adjusted into a Gaussian white noise model. This adjustment can be performed by an Anscombe's Transformation.

When training the de-noising method, multiple images of the phantom can be taken, wherein two or more of the phantom images have different signal to noise ratios. In such case, the direct wavelet transformation is applied to each phantom image to obtain a set of wavelet coefficients for each phantom image. Then, estimated parameters of the noise/background and the singularity distributions are obtained for each set of wavelet coefficients, and the parameters for an efficacious set of wavelet coefficients are saved for later use in de-noising a subject image. This process can be repeated for phantoms representing different body parts, such that a database of estimated parameters for different body parts is constructed; this database can be used to de-noise images of different subject body parts.

According to another aspect of the invention, there is provided a computer readable memory having recorded thereon statements and instructions for carrying out the de-noising method described above. Alternatively, an apparatus for de-noising a digital radiological image can be provided comprising means for carrying out each step in the above described method. In particular, the apparatus can be a digital radiography system comprising a scintillator, a digital camera optically coupled to the scintillator, and a computer in communication with the camera and programmed with statements and instructions for carrying out the de-noising method described above on digital images captured by the camera.

BRIEF DESCRIPTION OF THE FIGURES

FIGS. 8(a)-(c) kernel sizes equal to 2, 3, and 4 pixels, respectively.

DETAILED DESCRIPTION OF EMBODIMENTS OF THE INVENTION

Figure 1:
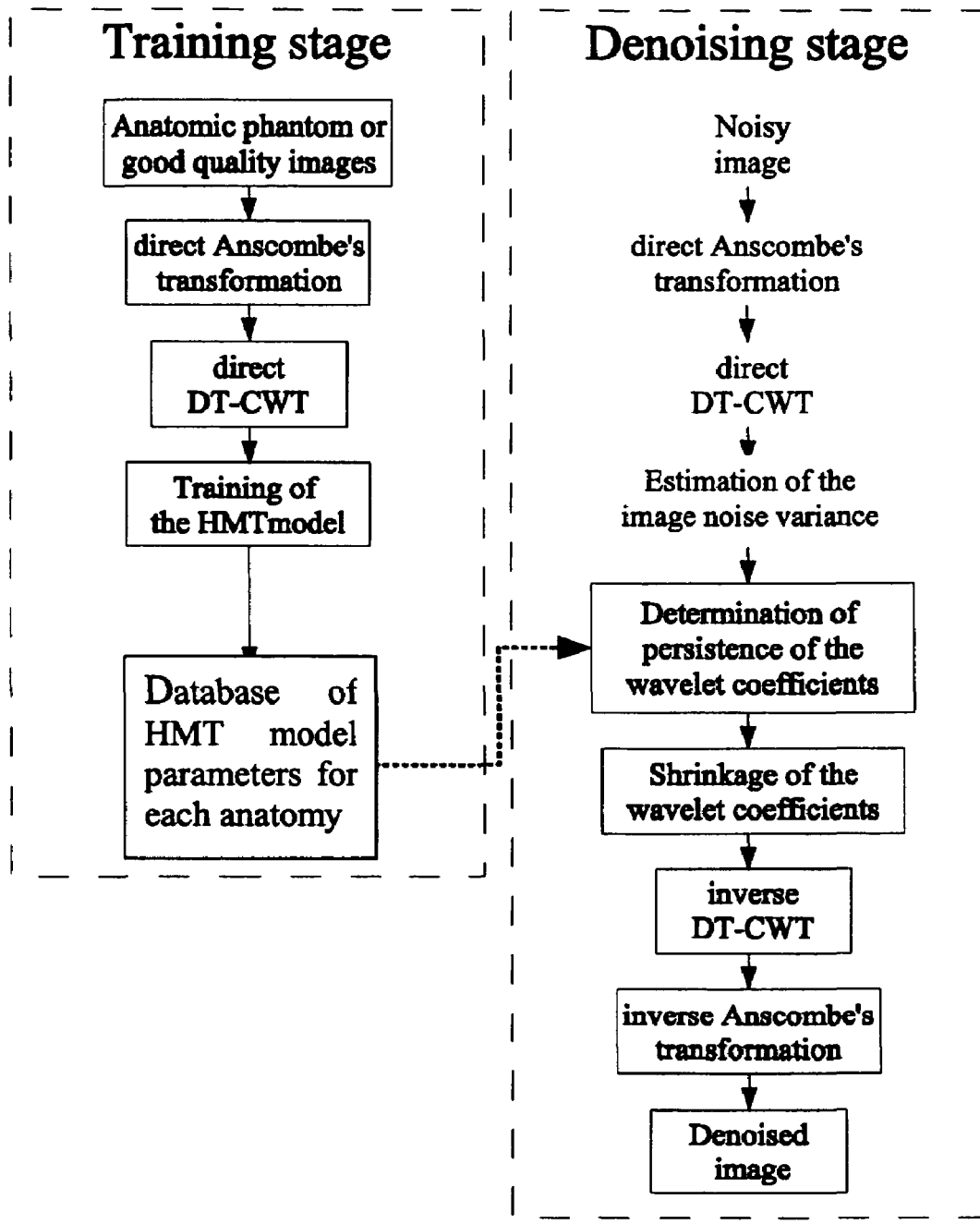
FIG. 1 is a flow chart of a method for de-noising digital radiographic images according to an embodiment of the invention.

According to one embodiment of the invention and referring to FIG. 1, a method for de-noising radiographic images starts by pre-processing an original image using Anscombe's variance stabilizing transformation, which acts as if the data arose from a Gaussian white noise model. The image is then decomposed in different sub-bands of frequency and orientation responses using an overcomplete dual-tree complex wavelet transform (DT-CWT). By using the DT-CWT, visual artifacts usually present in an image transformed by the traditional DWT are significantly minimized, with the advantage of having a task that is still tractable in terms of computation time. A Hidden Markov Tree (HMT) model is used to describe the correlation among the wavelet coefficients by modeling their marginal distribution and thus improving the discrimination between noisy and singularity pixels in an image. Finally, the modified wavelet coefficients are transformed back into the original domain in order to get the de-noised image. The efficacy of our method was demonstrated on both phantom and real digital radiographic images using quantitative and qualitative evaluation.

Figure 10:
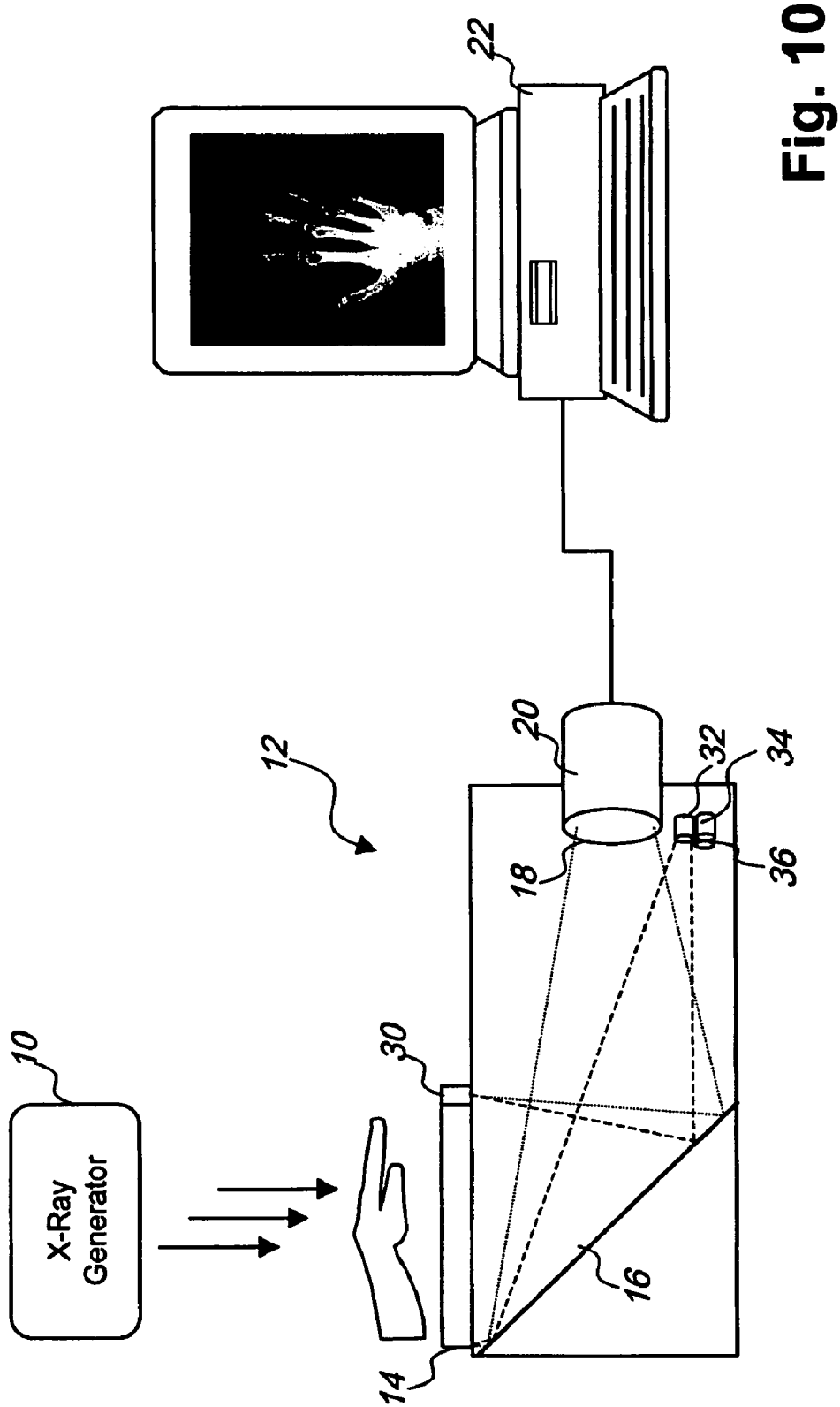
FIG. 10 is a schematic illustration of a digital radiographic system used with a preferred embodiment of the present invention.

Digital Radiographic (DR) System: The DR system used in our tests (referred as Xplorer™ system) is an optically coupled CCD based digital radiography unit. A schematic illustration of such a unit is shown in FIG. 10. Referring to FIG. 10, the digital radiography unit 12 comprises a CsI scintillator 14 as the primary x-ray conversion layer and couples the resulting light output to a CCD 20 by a mirror 16 and a lens 18 system. The 4K×4K CCD 20 is cooled to 263° K resulting in a dark current rate of less than one electron per pixel per second. Images are digitized at 14 bits and subsequently reduced for display to 12 bits. The Nyquist resolution is 4.61 p/mm. The CCD 20 is coupled to a computer 22, which receives and processes the images detected by the CCD 20. The wavelet-based de-noising method is encoded in a program stored on computer readable medium in the computer 22.

System DQE is very high at low frequencies but falls off at higher frequencies, requiring the use of sharpening algorithms. This inevitably boosts noise which can mask some features. The wavelet-based de-noising method is effective to reduce the noise in the images, as discussed in detail below.

Figure 2A:
FIG. 2(a) is a photograph of a phantom hand from Nuclear Associates.

Hand Phantom and Image Dataset: A hand phantom from Nuclear Associates as illustrated in FIG. 2(a) is comprised of human skeletal parts embedded in anatomically accurate, tissue-equivalent material. The materials have the same absorption and secondary radiation-emitting characteristics as living tissue. According to Nuclear Associates, all bone marrow has been simulated with tissue-equivalent material, which permits critical detail study of bone structure and sharpness comparisons using x-rays. In this work, the phantom was used to determine the characteristics of the image noise variance and the appropriate image set to be used in the training stage of the HMT model.

A total of fifteen radiographic images of lower and upper extremities (hands, feet, wrists and heels) were analyzed. All images were acquired using the same type of digital radiographic system, described above in the section "Digital Radiographic System", with 108 μn sampling interval and 12-bits gray-level quantization. The images used in this work were selected to characterize the best and worse quality images in terms of noise level.

Protocol for the Evaluation of Results: The proposed algorithm was evaluated quantitatively measuring the PSNR using digital radiographic images from the phantom illustrated in FIG. 2(a) and qualitatively using a set of fifteen clinical images.

The PSNR measure is defined as $$PSNR = 10 \log_{10}\left(\frac{\max(x_{i,j})}{\frac{1}{N}\sum_{i,j}(I_{i,j} - \hat{I}_{i,j})^2}\right), \quad (1)$$

where $I_{i,j}$ and $\hat{I}_{i,j}$ are the original and denoised images, respectively. $x_{i,j}$ is the pixel value in the spatial location (i,j) of the original image, and N is the total number of pixels in the image.

The qualitative analysis was assessed according to the opinion of two expert imaging specialists using a ranking table. The images were visually inspected on a computer 21" monitor. Image intensity histogram-equalization and image enhancement, using a standard unsharp-mask technique, were used for the sake of better visualization of the de-noising results. In addition, each processed image was visually compared to the same original image filtered using the Gaussian filter. The kernel size of the Gaussian was changed during the analysis to provide the best tradeoff between sharpness of the bone details and noise reduction. Table 1 was filled out for all fifteen images during the assessment of the algorithm.

TABLE 1

Example of the rank options and image characteristics analyzed which were used by the two imaging specialists to assess the results of the proposed de-noising algorithm.

| Image # Anatomy | Image characteristics being assessed | | | |
|---|---|---|---|---|
| | Noise reduction | Lack of artifacts | Quality of details | Sharpness |
| Soft tissue | | | | — |
| Bone details | | | | |

The images should be rated according to the following scores
1: excellent
2: good
3: average
4: poor
5: not acceptable Noise Modeling and Anscombe's Transformation: In digital radiographic systems there is a variety of imaging noise sources, which originate from the different stages and elements of the system, such as x-ray source, scattered radiation, imaging screen, CCD camera, and electronic circuits among others. The dominant cause of noise, however, is due to the quantum fluctuations in the x-ray beam. In the present method, a preprocessing stage is applied to the acquired images to correct for the impulse noise, CCD dark current noise and pixel nonuniformity.

It is well known that the Poisson distribution can be used to model the arrival of photons and their expression by electron counts on CCD detectors. Unlike Gaussian noise, Poisson noise is proportional to the underlying signal intensity, which makes separating signal from noise a very difficult task. Besides, well established methods for image de-noising, including the HMT model[2], are based upon the additive white Gaussian noise model. Therefore, in order to overcome this limitation, a variance stabilization (Anscombe's) transformation[13], described by $$I_A(x, y) = 2\sqrt{I(x, y) + \frac{3}{8}}, \quad (2)$$

is applied to the original noise image. I(x,y) and $I_A$(x,y) indicate the original and transformed images, respectively. The Anscombe's transformation acts as if the image data arose from a Gaussian white noise model. More precisely, as the number of photon counts increases, the noise variance in a square-root image tends to a constant, independent of the signal intensity. The inverse Anscombe's transformation is easily obtained by manipulating the above equation. In order to have a more tractable problem, in this method we are considering that the images are corrupted only by additive Poisson noise. Other sources of noise, including electronic noise normally present in digital radiographic systems, were not taken into account.

Dual Tree Complex Wavelet: Differently to the DWT, the dual-tree complex wavelet transform is a very attractive technique for medical image de-noising since it performs as well as the undecimated DWT, in the context of shift invariance, and with significantly lower computational cost.

Figure 3:
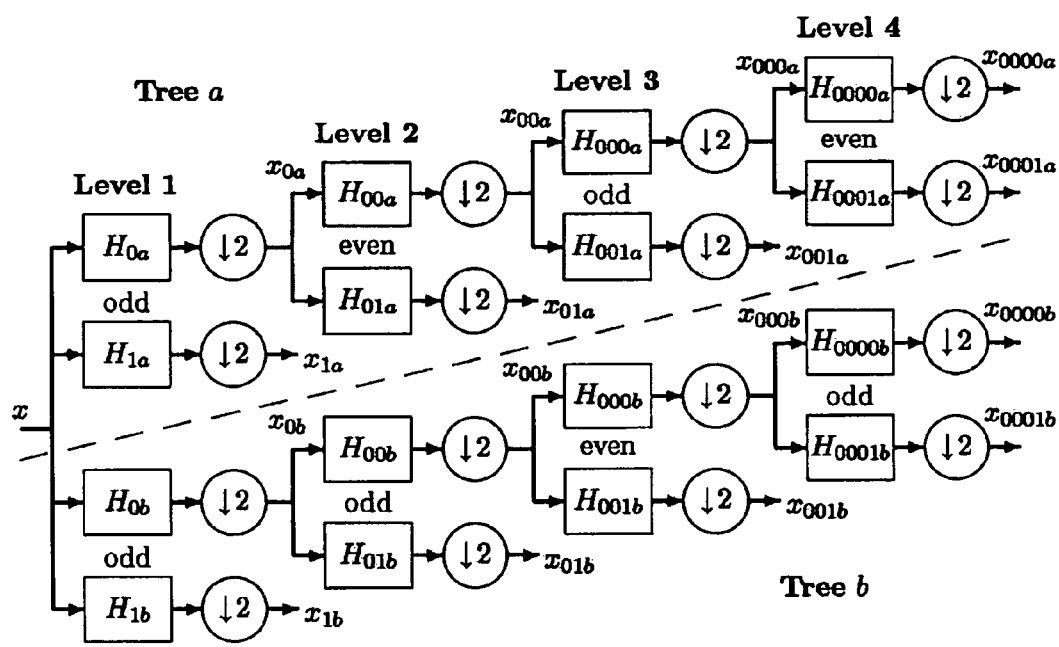
FIG. 3 is a schematic view of a dual-tree complex wavelet transform.

The nearly shift invariant property is obtained with a real biorthogonal transform having double the sampling rate at each scale and by computing parallel wavelet trees as illustrated in FIG. 3, which are differently subsampled. The DT-CWT presents perfect shift invariance at level 1, and approximate shift invariance, beyond this level. The DT-CWT also presents limited redundancy in the representation (4:1 for the 2D case—independent of the number of scales), good directional selectivity (six oriented subbands: ±15°, ±45°, ±75°), and it permits perfect image reconstruction.

Hidden Markov Tree Model in the Wavelet Domain: The HMT model, applied in the wavelet context, is a statistical model that can be used to capture statistical correlations between the magnitudes of wavelet coefficients across consecutive scales of resolution. The HMT works by modeling the following three important properties of the wavelet coefficients:

Non-Gaussian distribution: The marginal distribution of the magnitude of the complex wavelet coefficients can be well modeled by using a mixture of two-state Rayleigh distributions. The choice for using the Rayleigh mixture model instead of the Gaussian mixture model was based upon the fact that the real and imaginary parts of the complex wavelet coefficients may be slightly correlated, and therefore only the magnitudes of the complex wavelet coefficients will present a nearly shift-invariant property, but not the phase.

Figure 4:
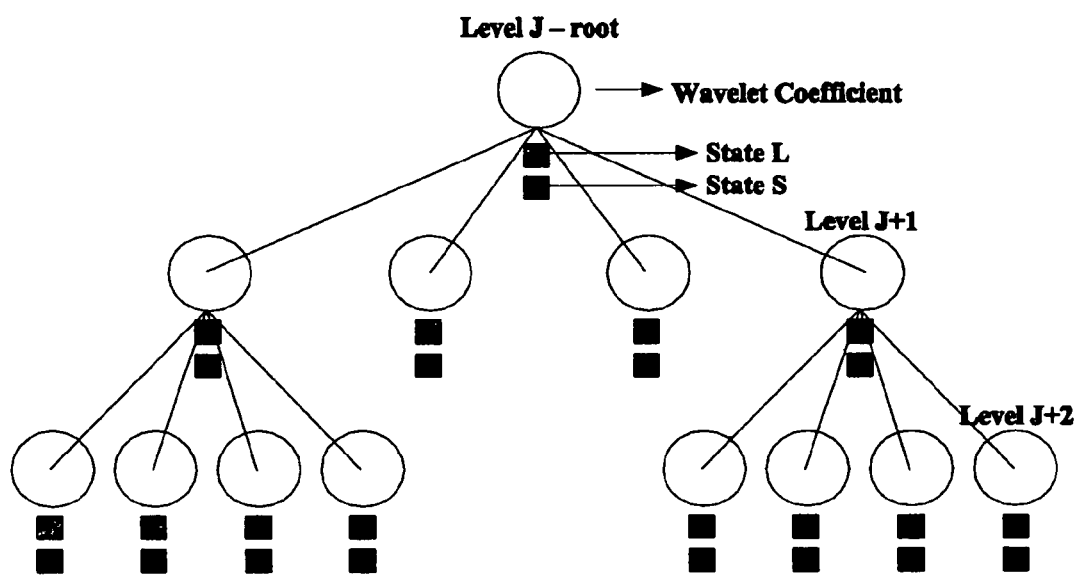
FIG. 4 is a 1D-tree structure graph for the dependencies of a Hidden Markov tree (HMT) model. Three levels are illustrated. The trees for the two internal wavelet coefficients in the level J+1 are not shown for the sake of better visualization.

Persistency: Large/small wavelet coefficients related to pixels in the image tend to propagate through scales of the quad-trees. Therefore, a state variable is defined for each wavelet coefficient which associates the coefficient with one of the two-state Rayleigh marginal distributions (one with small(S) and the other with large(L) variance). The HMT model is then constructed by connecting the state variables (L and S) across scales using the Expectation-Maximization (EM) algorithm. FIG. 4 shows the ID-structure of the Hidden Markov tree model.

Clustering: Adjacent wavelet coefficients of a particular large/small coefficient are very likely to share the same state (large/small).

The HMT model is parameterized by the conditional probability stating that the variable $S_j$ is in state m given $S_{p(j)}$ is in state n, or, $\epsilon_{j,p(j)}^{m,n}$=p($S_j$=m|$S_{p(j)}$=n) m, n=1, . . . , 2. The state probability of the root J is indicated by $p_{S,J}$(m)=p($S_j$=m) and the Rayleigh mixture parameters as $\mu_{j,m}$ and $\sigma_{j,m}^2$. The value of $\mu_{j,m}$ is set to zero because the real and imaginary parts of the complex wavelet coefficients must have zero means (wavelets have zero gain at dc). $\sigma_{j,m}^2$ is the variance. The parameters, grouped into a vector $\theta=\{p_{S,J}(m), \epsilon_{j,p(j)}^{m,n}, \sigma_{j,m}^2\}$, are determined by the EM algorithm proposed in [2]. Herein, we assume that the complex wavelet coefficients $w_j$ follow one of the two-state Rayleigh distributions as $$f(w_{j,m} | \sigma_{j,m}^2) = \frac{w_{j,m}^2}{\sigma_{j,m}^2} \exp\left(\frac{w_{j,m}^2}{2\sigma_{j,m}^2}\right), m = 1, 2. \quad (3)$$

In order to have a more reliable and robust (not biased) parameter estimation, the HMT model was simplified by assuming that all the wavelet coefficients and state variables within a particular level of a subband have identical parent-child relationships. Therefore, each of the six image subbands obtained by using the DT-CWT was trained independently and hence presents its own set of parameters. The magnitude of the complex wavelet coefficients for each subband were modeled by the resulting mixture model $$P(w_{j,m}) = \sum_{m=1,2} p_{SJ}(m) f(w_{j,m} | \sigma_{j,m}^2). \quad (4)$$

To take into account the dependencies among the wavelets coefficients of different scales, a tree-graph representing a parent-child relationship is used (see FIG. 4). The transition of a specific wavelet coefficient j between two consecutives levels in the tree is specified by the conditional probability $\epsilon_{j,p(j)}^{m,n}$. The algorithm for training the HMT model is known in the art, and for example, described in Crouse et. al. (1998) "Wavelet-based statistical signal processing using hidden Markov models", IEEE Transactions on Signal Processing 46:886-902.

Training the HMT Model: The main goal of the training stage is to find the correlation among the wavelet coefficients through the scales. Based upon experimental analysis and also in a practical laboratory experiment using the hand phantom object, we have verified that the best set of images to be used in the training stage of the HMT model should have the lowest level of noise and present enough image structure.

To validate the above statement, the hand phantom was imaged with different radiation levels, according to the parameters kVp, mAs as indicated in Table 2, given a set of five images with different SNR values. The images were used in turn to train the five models. The images were then processed and the PSNR was recorded for further evaluation. The results of the experiment are described below in a section titled "Results".

Selection of the clinical radiographic images used in the training of the HMT model was conducted by using a set of representative images (outside of the testing image-set) of each anatomy being studied (hand, foot, wrist and heel). A HMT model was estimated for each specific anatomy. The images were visually chosen based on the level of noise and amount of bone details. Images with lower level of noise and richer in bone details were given preference.

Noise Variance Estimation: Estimation of the noise variance is an important step in our image de-noising algorithm since it is used directly, along with the HMT parameters, in our wavelet-based filtering procedure. In the present work, the noise variance was estimated as $$\sigma_n^2 = \sqrt{\sigma_{real}^2 \times \sigma_{imaginary}^2} \qquad (5)$$

where $\sigma_{real}^2$ and $\sigma_{imaginary}^2$ are, respectively, the noise variance of the real and imaginary parts of the wavelet coefficients computed by using the median absolute deviation (MAD, [5]) algorithm.

TABLE 2

Figure 2B:
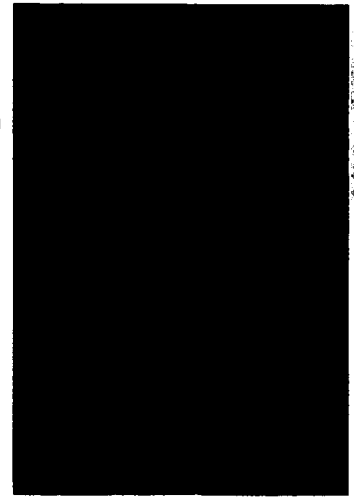
FIG. 2(b) is a radiographic image obtained from the hand phantom with 60 kVp, 3.2 mAs, SID=100 cm, small focal spot.

Parameters of the x-ray tube used in the experiment with the hand phantom shown in FIG. 2. In this experiment, the SID was set to 100 cm and the small focal spot was used. Except for the first set of parameters, the others are default values used in clinical application.

| Image | kVp | mAs | Type of patient usually applicable |
|---|---|---|---|
| 1 | 60 | 2.5 | pediatric |
| 2 | 60 | 3.2 | normal/medium |
| 3 | 60 | 4.0 | large |
| 4 | 60 | 20 | very high dose - NOT applicable |

De-noising Using the HMT. The de-noising procedure proposed in this work is composed of two shrinkage procedures: one is used for the levels 1 and 2, and the other for the subsequent levels. The rationality of this strategy is related to the fact that the DT-CWT provides perfect shift-invariance only at level 1, and approximate shift-invariance for the other levels. Because of that, the capture of the inter-scale dependencies among the wavelet coefficients using the HMT model starts to become unreliable beyond level 2 or 3, due to the considerable image energy variation.

For the first two levels of decomposition, the conditional mean estimation of the noise-free wavelet coefficient was obtained using $$\hat{w}_j = E[w_j | \theta] = \sum_j p(S_j = m | w_j, \theta) \frac{\sigma_{j,m}^2}{\sigma_{j,m}^2 + \sigma_n^2} w_j, \qquad (6)$$

where $p(S_j=m|w_j,\theta)$ is the probability of state m given the noise wavelet coefficient $w_j$ and the model parameters $\theta$ computed by the EM algorithm. $\sigma_n^2$ is the variance of the additive white Gaussian noise and E[ ] is the expectation operator.

Since the estimation of the subband variances $\sigma_{j,m}^2$ in the HMT model is performed using noise wavelet coefficients, their values are biased and should be corrected. The corrected estimation is then obtained by $$\sigma_{j,m}^2 = \begin{cases} \sigma_{j,m}^2 - \sigma_n^2, & \text{if } \sigma_{j,m}^2 > \sigma_n^2 \\ 0, & \text{otherwise} \end{cases} \qquad (7)$$

After level 2, a modified version of the soft-threshold procedure proposed in [10] was used to find the shrinkage factor $$c_j = \frac{sigm(S(\|w_j\| - T)) - sigm(-S(\|w_j\| + T))}{sigm(S(\max(\|w_j\|) - T)) - sigm(-S(\max(\|w_j\|) + T))}, \qquad (8)$$

which is applied to the real and imaginary parts of the complex wavelet coefficient $w_j$. In the above equation, $$sigm(y) = \frac{1}{1 + e^{-y}}$$

is the sigma function, S is an enhancement factor, and $T=\sigma_n/\beta$ is a threshold value. $\beta$ is considered as a smoothing parameter. In the present work the default values of S and $\beta$ were set to 1.3 and 0.9, respectively.

Figure 5:
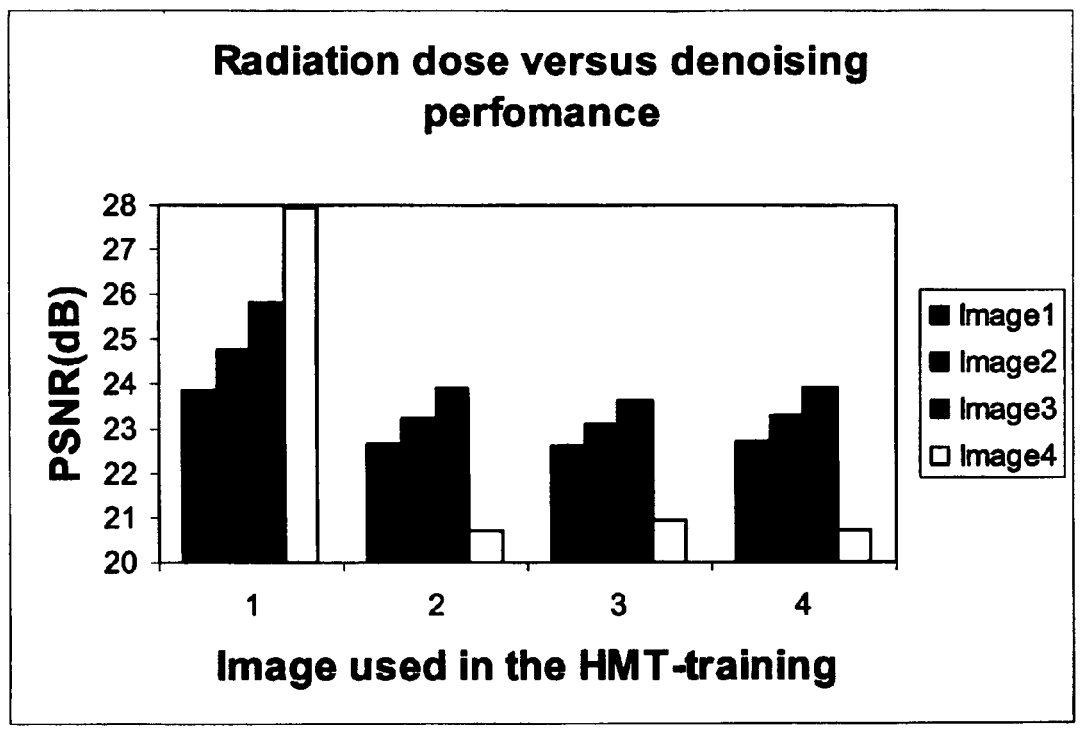
FIG. 5 is a graph of PSNR values resulting from the processing of four phantom images acquired using different exposure levels. Each image was used in turn to train a HMT model. Following, the estimated HMT models were used in the de-noising algorithm. The PSNR average values from column 1 to 4 in the attached table are 25.59, 22.64, 22.59, and 22.65, respectively.
Figure 6A:
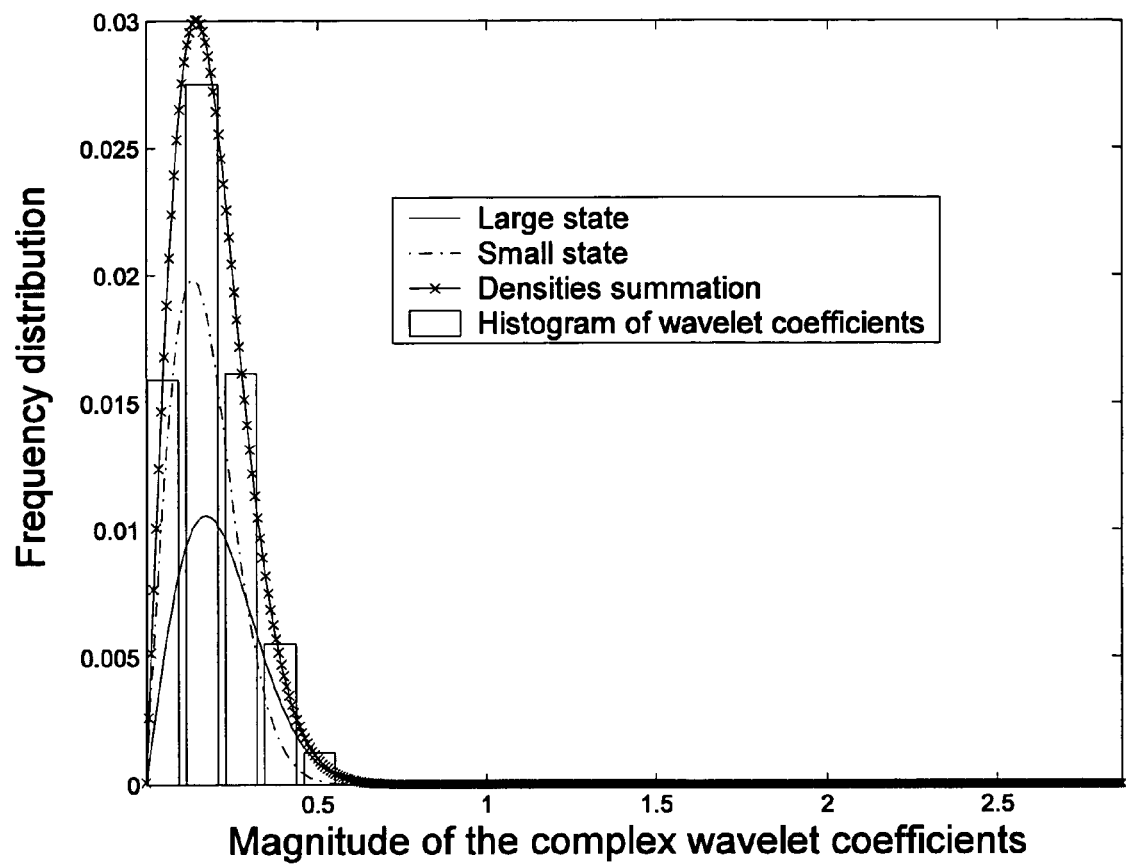
FIGS. 6(a) to (d) are examples of two-state Rayleigh mixture marginal distributions used to model the wavelet coefficients. The densities summation and the histograms of the wavelet coefficients are also shown. Plots were obtained for the first four levels (a-d); subbands with orientation 0°.
Figure 6B:
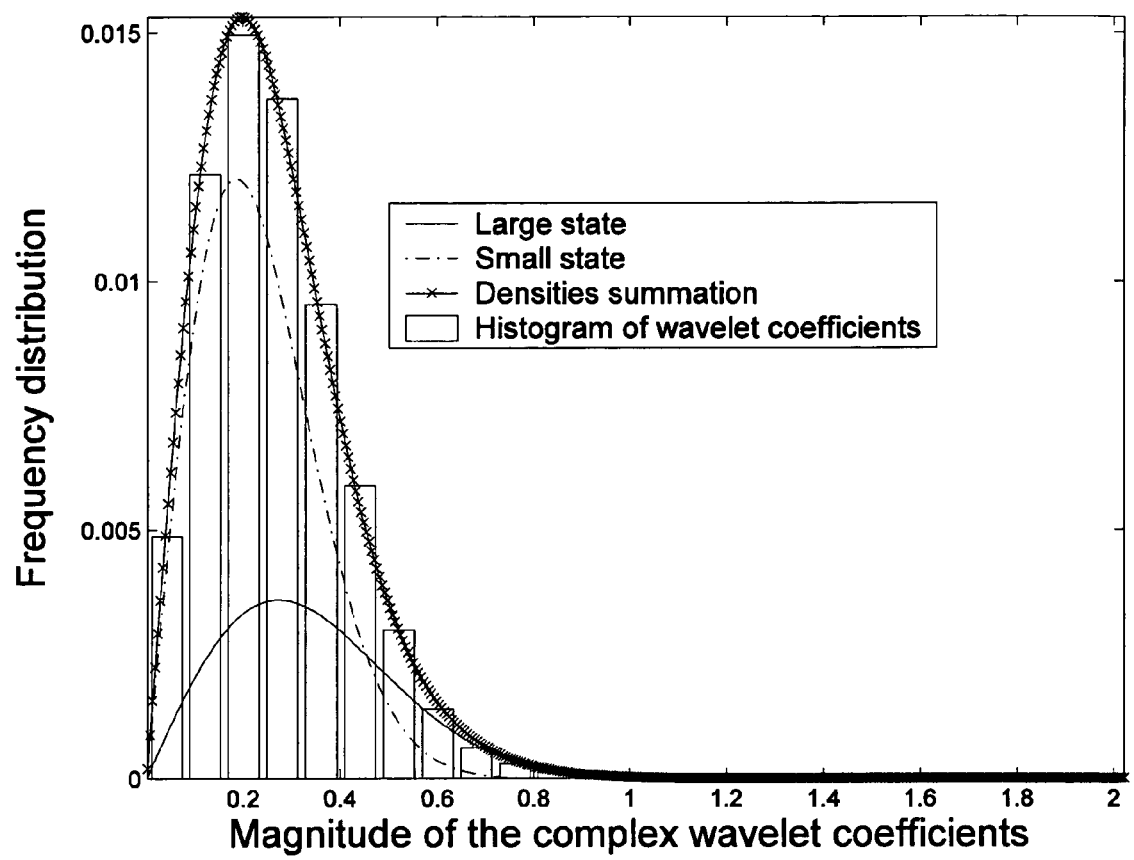
Figure 6C:
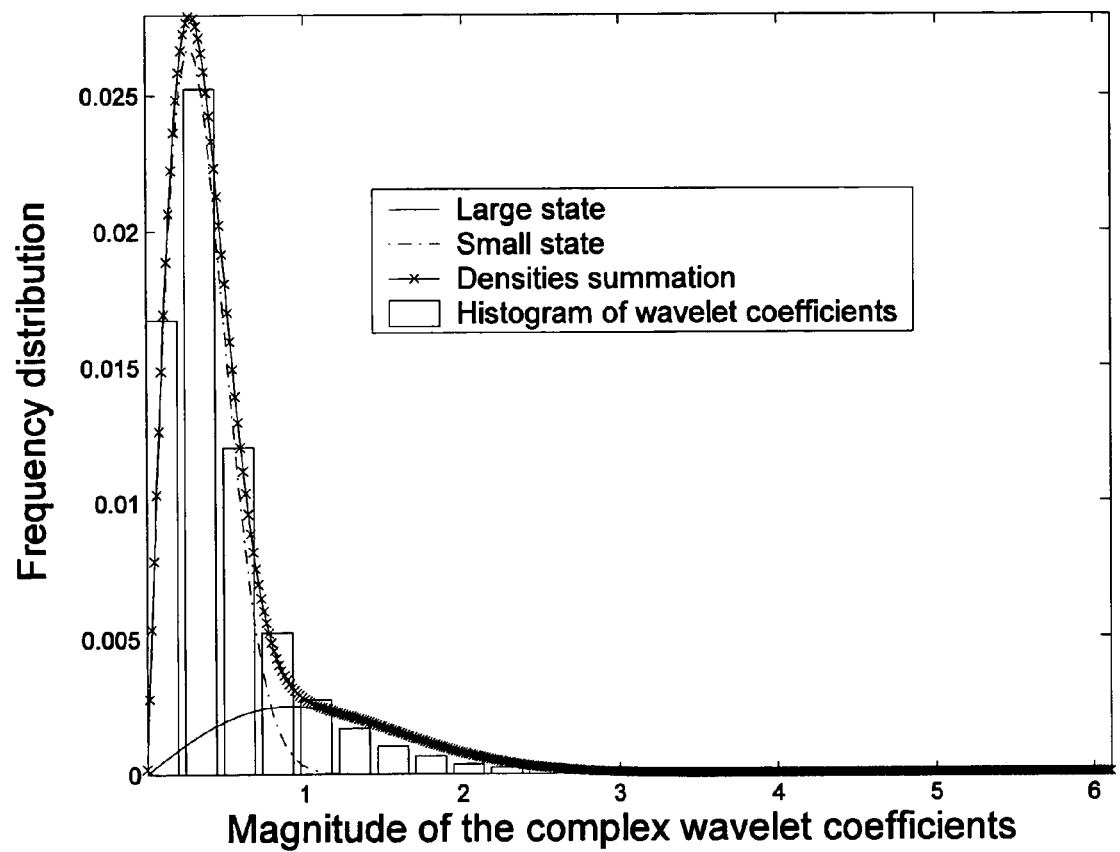
Figure 6D:
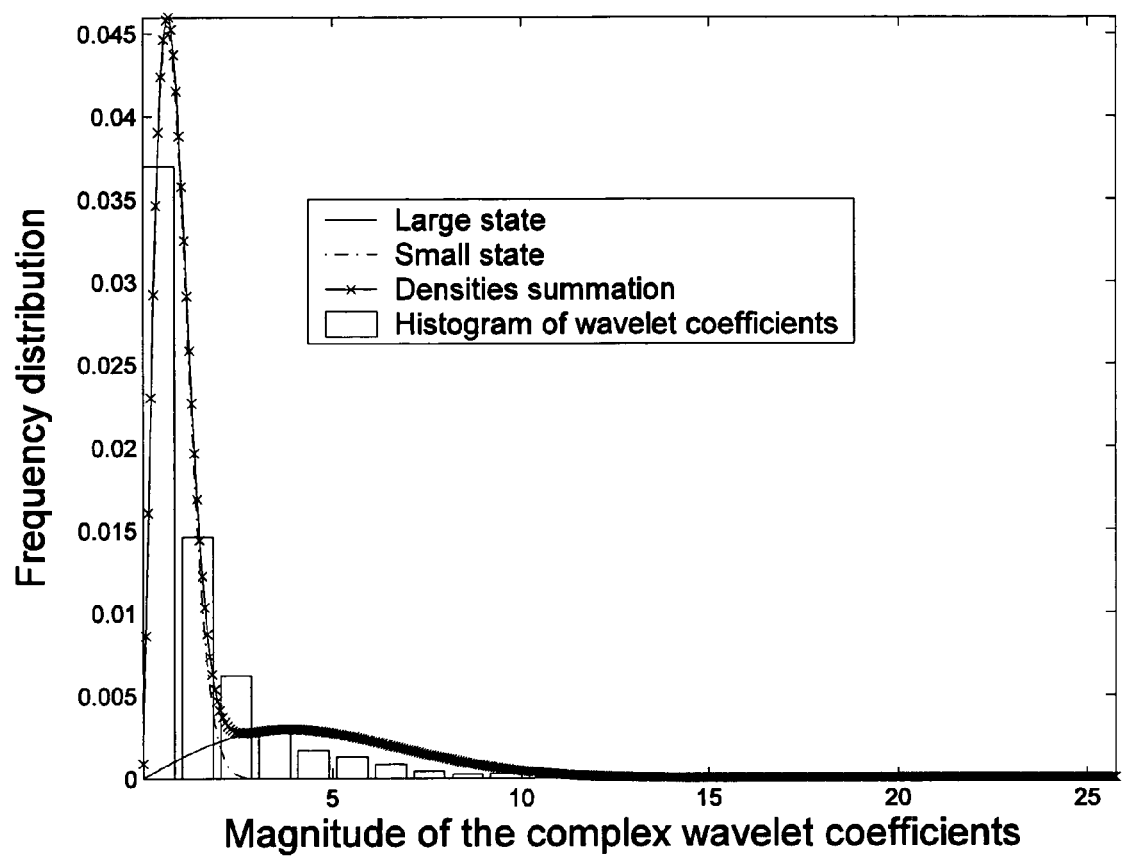

Results and Discussions: All the images illustrated in this section were post-processed using an image histogram equalization, and unsharp mask technique, for the sake of better visualization of the details. FIG. 5 shows the results of the experiment carried out to determine the relation between the radiation dose and the algorithm performance, in terms of PSNR The results were used to confirm that a high quality image (the one obtained with a high x-ray dose, 60 kVp and 20 mAs) is in fact the best option to be used in the training of the HMT model. By analyzing the average PSNR values we noticed that Image 3 (obtained with 60 kVp and 4.0 mAs) provides the second best average result. The worse choice would be Image 1, acquired with 60 kVp and 2.5 mAs. Despite the difference in the average values shown in FIG. 5, and except for Image 4, the PSNR values obtained by using different training images were very similar. The x-ray tube parameters used in the experiment are shown in Table 2.

Figure 2C:
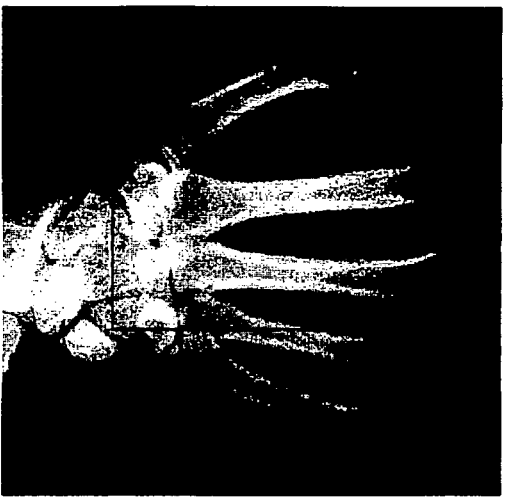
FIG. 2(c) is a clinical radiographic image denoised by the de-noising method shown in FIG. 1. The selected box in Figure (c) indicates the region area that will be zoomed in for sake of better visualization of the details of the denoised images.

FIG. 6 shows the results of the two-state Rayleigh mixture model fitting the marginal distribution of the wavelet coefficients for the first four consecutive levels (1 to 4) of the image in FIG. 2(c). Visual inspection indicates the good curve-fitting provided by the Rayleigh function. Due to the high image energy concentration around magnitude 0.25 in FIG. 6(a)-(b), application of a threshold technique to differentiate large/small values wavelet coefficients will not produce good results. Indeed, HMT-based de-noising algorithms usually outperform standard thresholding techniques because the degree of coefficient shrinkage is determined based not only upon the value of the coefficient but also upon its relationship with its neighbors across scales (quad-tree relationship).

Figure 7A:
FIGS. 7(a) to (c) are radiographic hand images of the image shown in FIG. 2(c) denoised by the de-noising method with different levels: (a) 2 levels, (b) 3 levels, and (c) 4 levels.
Figure 7B:
Figure 7C:
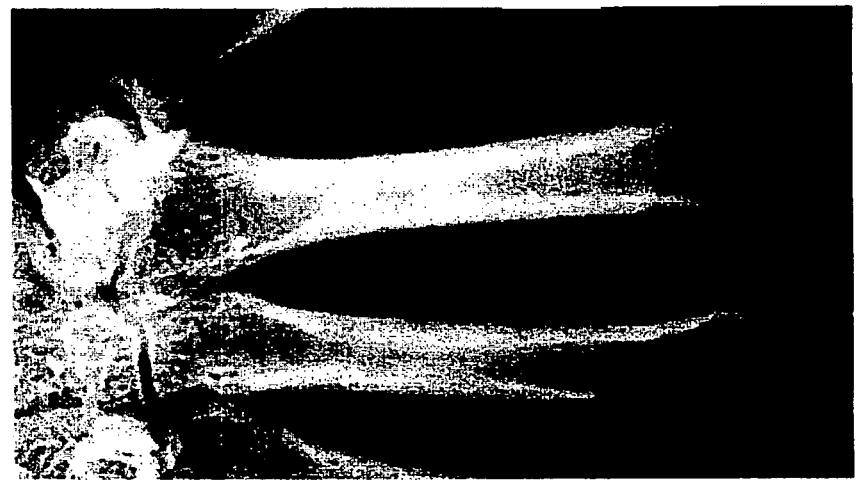
Figure 8A:
FIGS. 8(a) to (c) are radiographic hand images of the image shown in FIG. 2(c) denoised by a Gaussian filter with different kernel sizes.
Figure 8B:
Figure 8C:

For the sake of comparison, FIGS. 7 and 8 show examples of the radiographic hand image in FIG. 2(c) de-noised by using the proposed technique with different levels of de-noising and the Gaussian filter with different kernel sizes. In FIGS. 7(a) and 8(a), the granular appearance of the images is typical of images corrupted by quantum noise. In these cases, the Gaussian filter and the proposed algorithm using 2 levels of de-noising were not efficient in removing the noise. A huge improvement in reducing the quantum noise, however, is demonstrated in FIGS. 7(b) and (c). The soft-tissue is very clean and smooth compared to the results of the Gaussian filter in FIGS. 8(b) and (c). On the other hand, the amount of artifacts introduced close to the edges becomes more noticeable, compared to the results of the Gaussian filter. In general, the edges details are clearer and crisper in the images processed using the proposed technique (see FIG. 7(b)-(c) and FIG. 8(b)-(c) for comparison).

Figure 9:
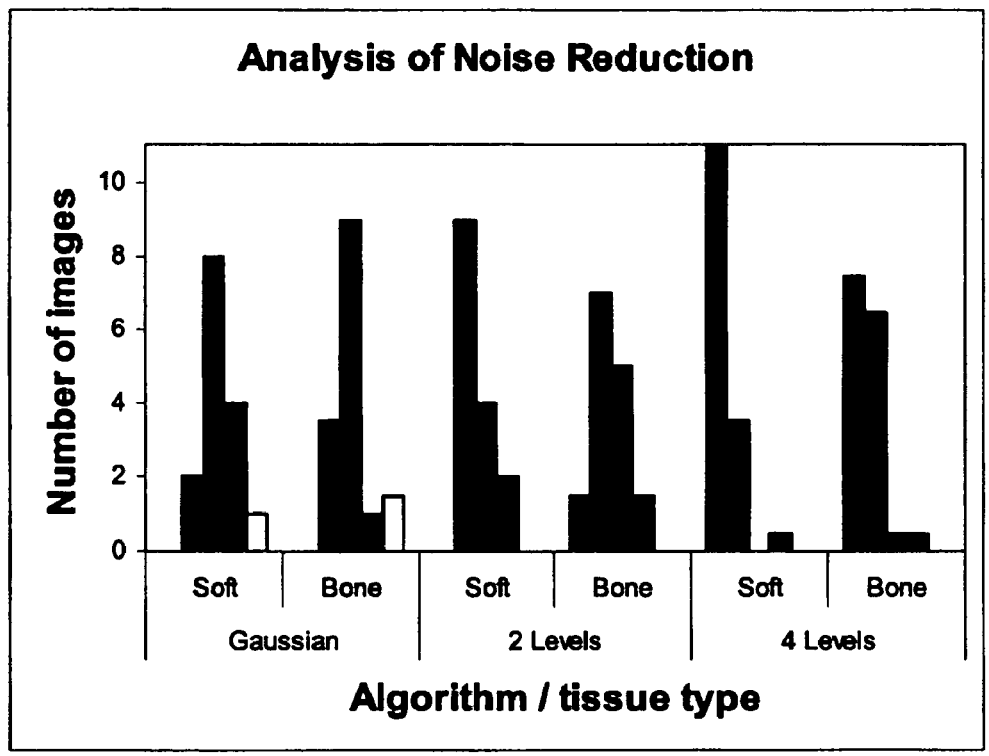
FIGS. 9(a) to (d) are graphs of average results of a qualitative assessment of the de-noising method. The graphs also provide a comparison with de-noising using the Gaussian filter. The assessment included: analysis of noise reduction (FIG. 9(a)), analysis of artifacts (FIG. 9(b)), quality of details (FIG. 9(c)), and analysis of bone sharpness (FIG. 9(d)).
Figure 9B:
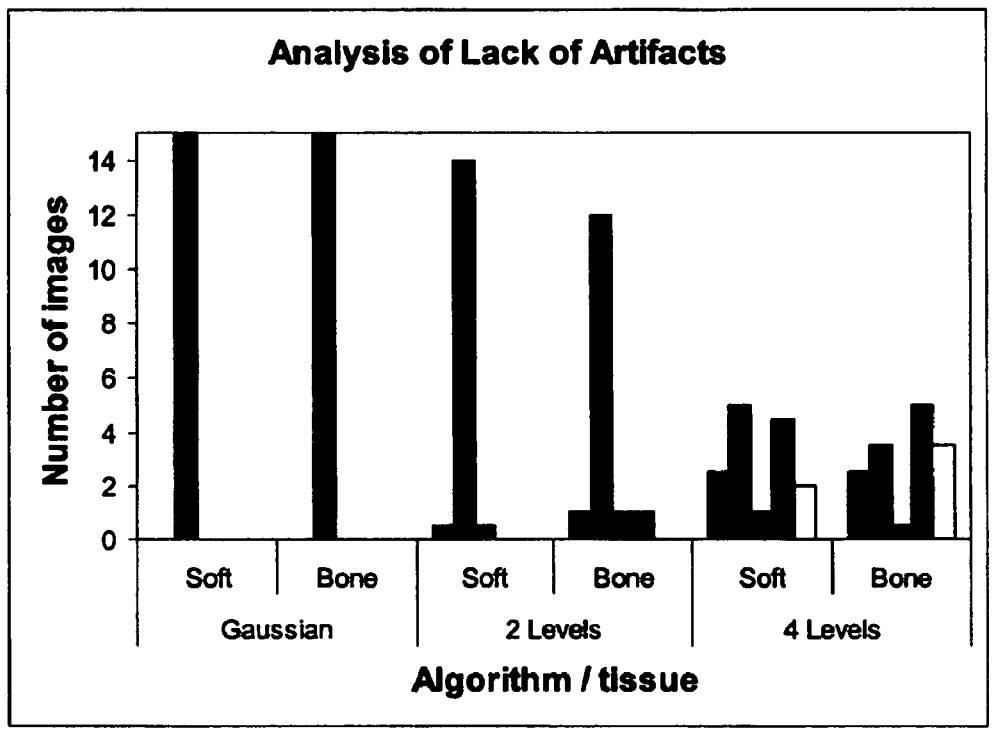
Figure 9C:
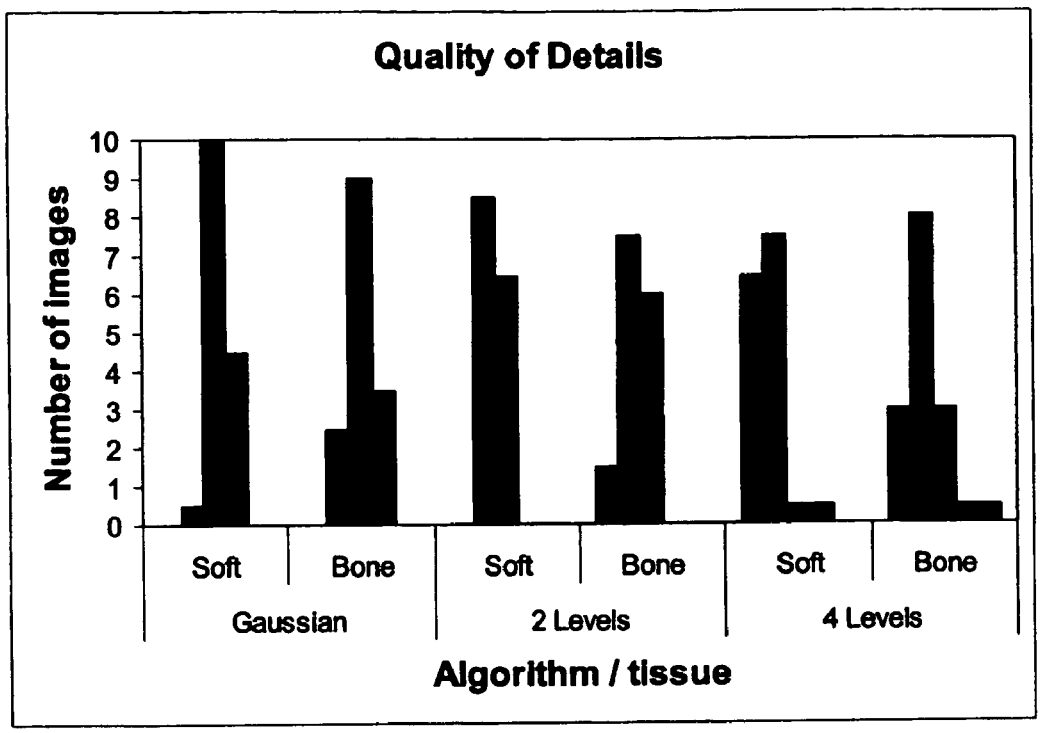
Figure 9D:
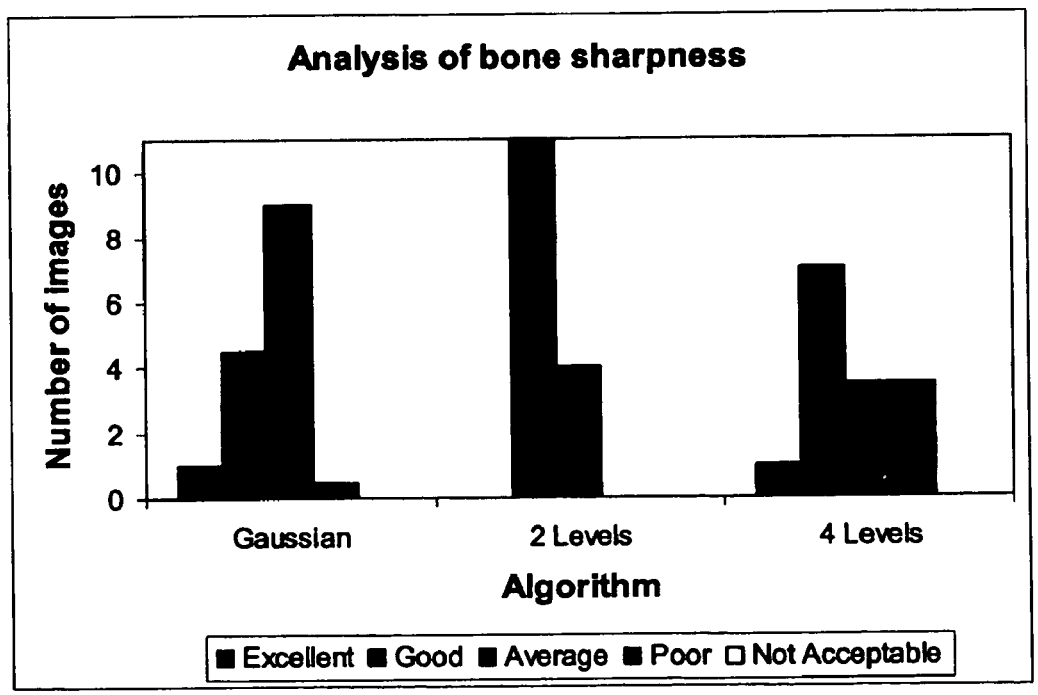

The results obtained from the de-noising of the fifteen clinical digital radiographs were analyzed and are shown in FIG. 9. In FIG. 9(a) we confirm the excellent performance of the algorithm, using 2 and 4 levels, in reducing noise of both soft-tissue and bone. As pointed out by the two specialists who analyzed the images, the algorithm was able to remove with great success the quantum noise. Despite the good performance in noise reduction, the proposed algorithm presented a poorer performance in regarding to the absence of artifacts, when using 4 levels de-noising, according to FIG. 9(b). The artifacts are mostly caused by the pseudo-Gibbs phenomenon appearing near strong edges. This undesirable effect becomes predominant as the number of denoised scales increases. The proposed algorithm also scored well on overall quality of details after de-noising, as can be seen in FIG. 9(c). The bone sharpness was also preserved when compared to the Gaussian filter in FIG. 9(d). Except for the presence of artifacts, the proposed de-noising algorithm using 4 level de-noising presented better performance than the same method using 2 level de-noising or the Gaussian filter.

While the preferred embodiments of the invention has been illustrated and described, it will be appreciated that various changes can be made therein without departing from the scope and spirit of the invention.

What is claimed is:

1. A method of de-noising a digital radiological image comprising:
   (a) obtaining a digital radiological image of a subject;
   (b) applying a dual-tree complex wavelet transformation to the subject image to obtain wavelet coefficients of the subject image;
   (c) shrinking or thresholding the wavelet coefficients of the subject image to reduce noise components using estimated parameters of a noise and background distribution and a singularity distribution, the estimated parameters fitting an observed overall distribution of wavelet coefficients of a phantom derived from a direct wavelet transformation of a digital radiological image of the phantom using a Hidden Markov Tree model; and
   (d) applying an inverse wavelet transformation to the shrunk or thresholded wavelet coefficients to obtain a de-noised subject image.

2. A method as claimed in claim 1 further comprising adjusting the subject image into a Gaussian white noise model before applying the wavelet transformation to the subject image.

3. A method as claimed in claim 2 wherein the adjustment of the subject image into a Gaussian white noise model is performed by an Anscombe's transformation.

4. A method of claim 1 wherein the estimated parameters are efficacious estimated parameters selected from a group of estimated parameters associated with a group of phantom images each having a different signal to noise ratio.

5. An apparatus for de-noising a digital radiological image comprising:
   (a) means for obtaining a digital radiological image of a subject;
   (b) means for adjusting the subject image into a Gaussian white noise model;
   (c) means for applying a dual-tree complex wavelet transformation to the adjusted subject image to obtain wavelet coefficients of the subject image;
   (d) means for shrinking or thresholding the wavelet coefficients of the subject image to reduce noise components using estimated parameters of a noise and background distribution and a singularity distribution, the estimated parameters fitting an observed overall distribution of wavelet coefficients of a phantom derived from a direct wavelet transformation of a digital radiological image of the phantom using a Hidden Markov Tree model; and
   (e) means for applying an inverse wavelet transformation to the shrunk or thresholded wavelet coefficients to obtain a de-noised subject image.

6. A computer readable memory having recorded thereon statements and instructions for execution by a computer to carry out the method of claim 1.

7. A method of de-noising a digital radiological image comprising:
   (a) obtaining a digital radiological image of a subject;
   (b) applying a direct wavelet transformation to the subject image to obtain wavelet coefficients of the subject image;
   (c) shrinking or thresholding the wavelet coefficients of the subject image to reduce noise components using estimated parameters of a noise and background distribution and a singularity distribution, the estimated parameters fitting an observed overall distribution of wavelet coefficients of a phantom derived from a direct wavelet transformation of a digital radiological image of the phantom; and
   (d) applying an inverse wavelet transformation to the shrunk or thresholded wavelet coefficients to obtain a de-noised subject image.

8. A method as claimed in claim 7 wherein the direct wavelet transformation of the phantom image is a dual-tree complex wavelet transformation.

9. A method as claimed in claim 7 wherein the direct wavelet transformation of the subject image is a dual-tree complex wavelet transformation.

10. A method as claimed in claim 7 wherein a Hidden Markov Tree model is used to perform the direct wavelet transformation of the digital radiological image of he phantom.

11. A method as clamed in claim 10 comprising adjusting the subject image into a Gaussian white noise model prior to applying the direct wavelet transformation to the subject image.

12. A method as claimed in claim 11 wherein the adjustment of the subject image into a Gaussian white noise model is performed by an Anscombe's transformation.

13. An apparatus for de-noising a digital radiological image comprising:
   (a) means for obtaining a digital radiological image of a subject;
   (b) means for applying a direct wavelet transformation to the subject image to obtain wavelet coefficients of the subject image;
   (c) means for shrinking or thresholding the wavelet coefficients of the subject image to reduce noise components using estimated parameters of a noise and background distribution and a singularity distribution, the estimated parameters fitting an observed overall distribution of wavelet coefficients of a phantom derived from a direct wavelet transformation of a digital radiological image of the phantom; and (d) means for applying an inverse wavelet transformation to the shrunk or thresholded wavelet coefficients to obtain a de-noised subject image.

14. A computer readable memory having recorded thereon statements and instructions for execution by a computer to carry out the method of claim 7.

* * * * *